United States Patent
Läuger et al.

(10) Patent No.: US 8,453,496 B2
(45) Date of Patent: Jun. 4, 2013

(54) RHEOMETER AND RHEOMETRIC METHOD FOR TESTING SAMPLES

(75) Inventors: Jörg Läuger, Stuttgart (DE); Michael Krenn, Zettling (AT)

(73) Assignee: Anton Paar GmbH, Graz-Strassgang (AT)

( * ) Notice: Subject to any disclaimer, the term of this patent is extended or adjusted under 35 U.S.C. 154(b) by 309 days.

(21) Appl. No.: 12/916,777

(22) Filed: Nov. 1, 2010

(65) Prior Publication Data
US 2011/0100098 A1    May 5, 2011

(30) Foreign Application Priority Data
Oct. 30, 2009   (AT) ............................... A 1722/2009

(51) Int. Cl.
*G01N 11/14*   (2006.01)

(52) U.S. Cl.
USPC ....................................... 73/54.28

(58) Field of Classification Search
USPC ............ 73/54.01, 54.02, 54.28, 54.31, 54.32, 73/54.33, 54.34, 54.35, 54.37, 54.39
See application file for complete search history.

(56) References Cited

U.S. PATENT DOCUMENTS

| | | | | |
|---|---|---|---|---|
| 5,357,783 A * | 10/1994 | Eschbach | ..................... | 73/54.33 |
| 6,571,610 B1 * | 6/2003 | Raffer | ........................ | 73/54.35 |
| 2006/0000262 A1 * | 1/2006 | Raffer | ........................ | 73/54.28 |
| 2008/0022758 A1 * | 1/2008 | Cottais et al. | ............... | 73/54.32 |
| 2010/0269571 A1 * | 10/2010 | Raffer | ........................ | 73/54.28 |

* cited by examiner

*Primary Examiner* — Hezron E Williams
*Assistant Examiner* — David Z Huang
(74) *Attorney, Agent, or Firm* — Laurence A. Greenberg; Werner H. Stemer; Ralph E. Locher

(57) ABSTRACT

A method for testing samples uses a rheometer in which a measuring shaft bearing a first measuring part is rotated by a motor and the sample is introduced into a measuring gap between the first measuring part and a further measuring part. The further measuring part is mounted on a further, driven measuring shaft and the two measuring parts are rotated or oscillated at a predetermined speed independently of one another, or brought to a standstill. At the same time or in rapidly succeeding intervals during the same measuring process, the torque and the normal force are determined by a first moment detector and the first measuring unit, and the normal force exerted by the sample on the further measuring part and/or the further measuring shaft and the torque exerted on the further measuring shaft by means of a further separate motor rotating said measuring shaft are determined by means of a further measuring unit and a further moment detector and in that said simultaneously determined measured values are supplied for evaluation.

15 Claims, 5 Drawing Sheets

RHEOMETER AND RHEOMETRIC METHOD FOR TESTING SAMPLES

CROSS-REFERENCE TO RELATED APPLICATION

This application claims the priority, under 35 U.S.C. §119, of Austrian patent application A 1722/2009, filed Oct. 30, 2009; the prior application is herewith incorporated by reference in its entirety.

BACKGROUND OF THE INVENTION

Field of the Invention

The invention relates to a method for testing samples using a rheometer and to a rheometer. In the sample-testing method, a measuring shaft of the rheometer which bears a first measuring part is rotated by way of a motor. The sample is introduced into a measuring gap formed by the first measuring part and a further measuring part. The two measuring parts are rotated relative to one another and the torque of the motor is determined by way of a moment detector and the normal force exerted by the sample on the first measuring part is determined by a first measuring unit. The rheometer is of the type having a measuring shaft driven by a motor and bearing a first measuring part, a measuring gap for the sample defined by the first measuring part and a further measuring part, a moment detector for detecting the torque of the motor and a measuring unit for determining the normal force exerted by the sample on the measuring shaft and/or the first measuring part Rotary rheometers and oscillating rheometers are instruments for determining the flow behavior of visco-elastic samples, for example in tests for rotation, creep, relaxation and oscillation. In this context, both the flow behavior of fluids and the deformation behavior of solids may be tested. Generally, real samples exhibit a combination of elastic and plastic behavior. The sample material to be tested, as in the case according to the invention, is introduced into the measuring chamber between two measuring parts and by adjusting the height of the measuring parts and the corresponding sensors, the gap height is set and/or determined. The upper or lower measuring parts are set in rotational movement relative to one another about a common rotational axis and the sample is subjected to a shear load by rotating the measuring parts relative to one another. Thus both rotating and rotating-oscillating movements are possible. The measuring parts may have different geometries; for example, plate-plate measuring systems, concentric cylinder measuring systems, cone-plate-measuring systems and specific arrangements are known for different fields of application, for example for measuring the immobilization behavior of dispersions or building materials, electro-rheological measurements, etc.

The torque may be determined by a motor designed both for driving and determining the torque or via two motor units separate from one another for driving/rotation or determining the torque, which are assigned in each case to one of the measuring parts.

The torque is generally measured via the current consumption of an electric motor. Depending on the motor used and/or type of device, for the torque M the following applies:

$$M = c_1 I \text{ or } M = c_2 I^2$$

where $c_1$ and/or $c_2$ are device-specific constants.

FIGS. 1 and 1A show two prior art rheometer configurations of different designs. A sample 19 to be measured is located in the measuring gap 1 between the two measuring parts 1a and 1b which, located at a defined distance 1 from one another, determine the gap height. The two figures show a plate-plate measuring system; any variant may be used, such as cone-plate-measuring systems, cylinder systems, or modifications thereof for very different applications; accordingly, only the geometric data has to be taken into account in the evaluation of the results. The respective measuring parts may be easily fastened and replaced by means of couplings for the measuring body; in some instances the geometric and calibration data are stored on the measuring body and may thus be automatically transmitted to the evaluation unit.

FIG. 1 shows a rheometer with separate devices for driving and for measuring the torque. A drive motor 2a moves the lower measuring part 1b via a shaft 3a in a rotational or oscillating manner, while the effective torque is determined on the upper measuring part 1b via the separate torque sensor 4 and namely by means of a measuring motor 2b relative to the shaft 3b. The shaft 3b is connected to the drive motor 2b via a coupling 31. In this case, the regulation is carried out at the resting position of the upper measuring part 1a and the effective torque is thus proportional to the current consumption of the motor 2b.

In the embodiment according to FIG. 1a, a normal force sensor 6 is provided on the air bearing. In the embodiment according to FIG. 1a, normal force sensors are provided on the measuring part 1b. All of the measurement sensors are queried by an evaluation and control unit 8 and the measurement signals received therefrom are evaluated. In a rheometer according to FIG. 1a with a combined driving and measuring device and according to FIG. 1 with separate devices for the driving and measuring, for determining the rheological parameters of the substance to be tested, the ratio between the torque acting on the axle and the supply parameters of the motor is known by calibration and is present in the evaluation unit 8.

A combined driving and measuring motor CMT (combined motor transducer) rotates the measuring and drive shaft 3. The position sensor 4 measures the rotational angle and/or the time and thus the speed.

The bearing 5 substantially comprises a stator 51 fixed to the stand and/or housing and a rotor and/or supporting flange 40 rotatably mounted therein, which is fixedly connected to the measuring shaft 3 and/or the shaft 3b. The supporting flange 40 serves for absorbing the axial loads acting on the shafts 3 and/or 3b, in particular the weight of the shafts and measuring parts and is supported relative to the stator 51 by means of through-flowing air. The supply devices as well as the feed lines and discharge lines for the air are not shown. The use of other bearings which are as free as possible from friction, such as for example magnetic bearings, is possible and equivalent to the use of air bearings.

In the embodiment according to FIG. 1a, a normal force sensor 6 is provided on the air bearing. In the embodiment according to FIG. 1a, normal force sensors 7 are provided on the measuring part 1b. All of the measurement sensors are queried by an evaluation and control unit 8 and the measurement signals received therefrom are evaluated. In a rheometer according to FIG. 1a with a combined driving and measuring device and according to FIG. 1 with separate devices for the driving and measuring, for determining the rheological parameters of the substance to be tested, the ratio between the torque acting on the axle and the supply parameters of the motor is known by calibration and is present in the evaluation unit 8.

The measured values which are obtained are combined in the evaluation unit 8 with the sample temperature, with the height of the measuring gap 1 as well as with the device constants in a manner known per se and the rheological data of the sample 19 of the medium may be calculated therefrom. From the measured data, current consumption and/or frequency and/or phase position and the geometric data, the rheological measured values, shear stress T [Pa] and shear rate γ [s−1] are calculated by means of the evaluation unit 8 and the viscosity η=γ/T determined therefrom. These values are displayed in a display unit or are available as data sets for further use in data processing systems.

The configuration shown in FIG. 1a makes it possible, depending on the query, to perform tests with Controlled Shear Rate (CSR test) and tests with Controlled Shear Stress (CSS tests).

Controlled Shear Rate (CSR) means predetermining the speed and measuring the torque. This process is used, for example, for determining the flow behavior at a defined speed. This method is generally applied in samples which have no yield point, i.e. they flow automatically.

In the Controlled Shear Stress (CSS) test, the sample is subjected to a defined load by predetermining the torque and the resulting speed and/or rotational angle are measured. This process is used, for example, when determining the yield point.

Both types of test may be performed in the form of shear tests by oscillating movement about the rotational axis and, for example in the CSR test, via the amplitude and phase position of the torque, provide accurate information about loss factors and complex shear modulus.

In any case, an electronic control and/or regulating unit ensures that the predetermined test parameters for speed or torque are maintained. Modern rheometers are provided with digital control processors, which only require milliseconds for a closed-loop control circuit.

Normal force sensors 7 which are additionally provided are able to measure the normal forces present using different measuring principles, for example piezo sensors, optical methods, amongst others, and using different attachment sites, for example on the air bearing 5, on a measuring part 1a, 1b or on the stand of the rheometer, and monitor the elastic behavior of the sample.

Devices with a separate driving and measuring unit according to FIG. 1 require greater complexity of the regulation as the measuring element has to be held over the measuring motor in the initial position.

To this end, in this configuration, only the response moment of the sample may be measured; the inertia of the drive motor, which is measured in any event in the case of the combined motor and has to be corrected at that point due to its calibration data, is not relevant here.

The configurations according to FIG. 1 and/or FIG. 1a thus exhibit advantages in each case, but also limitations where there are different measuring methods.

SUMMARY OF THE INVENTION

It is accordingly an object of the invention to provide a rheometer and a rheometric testing method which overcome the above-mentioned disadvantages of the heretofore-known devices and methods of this general type and which combines the advantages of the two measuring systems into one system. A further object is an extension of the possible measuring range of rotary rheometers to obtain more accurate measurements at higher speeds. Higher speeds and thus higher shear rates are necessary when simulating the behavior of a plurality of samples, for example dyes for injection-molding processes.

With the foregoing and other objects in view there is provided, in accordance with the invention, a rheometric testing method, which comprises:

providing a rheometer having a measuring shaft bearing a first measuring part, a first motor for rotating the first measuring shaft, a second measuring shaft bearing a second measuring part disposed to form a measuring gap together with the first measuring part, and a second motor for rotating the second measuring shaft;

introducing a sample to be tested into the measuring gap formed between the first measuring part and the second measuring part;

rotating or oscillating the first and second measuring parts relative to one another at a predetermined speed independently of one another, or bringing to a standstill independently of one another, and thereby determining a torque of the motor by way of a moment detector and detecting a normal force exerted by the sample on the first measuring part by way of a first measuring unit;

simultaneously, or in rapidly successive intervals during the same measuring process, determining the torque and the normal force by way of the first moment detector and the first measuring unit, and determining a normal force exerted by the sample on the second measuring part and/or the second measuring shaft and the torque exerted on the second measuring shaft by the second motor rotating the second measuring shaft by way of a second measuring unit and a second moment detector; and supplying the simultaneously determined measured values for evaluation and outputting the evaluated test results pertaining to the respective sample.

In a method for testing samples using a rheometer, in which a measuring shaft bearing a first measuring part is rotated by means of a motor for the rotation, the sample being introduced into a measuring gap formed by the first measuring part and a further measuring part, and the two measuring parts being rotated relative to one another and the torque of the motor being determined by means of a moment detector and the normal force exerted by the sample on the first measuring part being determined by means of a first measuring unit, these objects are achieved according to the invention in that the first measuring part and the further measuring part mounted on a further measuring shaft for testing the sample are in each case rotated or oscillated at a predetermined speed independently of one another, or brought to a standstill, in that at the same time, preferably at exactly the same time or at rapidly succeeding intervals during the same measuring process, the torque and the normal force are determined by means of the first moment detector and the first measuring unit, and the normal force exerted by the sample on the further measuring part and/or the further measuring shaft and the torque exerted on the further measuring shaft by means of a further separate motor rotating said measuring shaft are determined by means of a further measuring unit and a further moment detector, and in that said simultaneously determined measured values are supplied for evaluation, in particular combined evaluation.

In a rheometer comprising a measuring shaft driven by a motor and bearing a first measuring part, a measuring gap for the sample defined by the first measuring part and a further measuring part, a moment detector for detecting the torque of the motor and a measuring unit for determining the normal force exerted by the sample on the measuring shaft and/or the first measuring part, these objects are achieved according to the invention, in that a further measuring shaft and/or the rotational axis of a further measuring shaft driven by a further separate motor is mounted aligned with the measuring shaft and/or on the rotational axis of said measuring shaft, on which a further measuring part may be fastened and/or is fastened, in that for determining the torque exerted by the further motor a further moment detector is provided, and in that for determining the normal force exerted by the sample on the further measuring part and/or the further measuring shaft, a further measuring unit is provided. The measured values are supplied to an evaluation unit.

A specific advantage of the procedure according to the invention is that greater accuracy may be achieved at low speeds, for example by both motors being permitted to run in the same direction with a desired difference in speed. As a result of the greater absolute speed of the two motors, a greater angular range is covered in a shorter time and thus an average may be calculated more easily, for example over an entire revolution.

Generally, the tests which may be carried out using the previous rheometers may be carried out with the greatest accuracy. The torque from the sample counteracting shear forces and/or movement of a measuring part, naturally acts equally on the surfaces of both measuring parts, and the torque values determined using both measuring motors increase the accuracy of the system when an average value is calculated. Furthermore, tests are also possible using rotational movements of both measuring parts in the same and/or opposing direction, by oscillating both measuring parts and combining the rotation and oscillation of one respective measuring part. Primarily, however, it is advantageous, in particular for increasing the accuracy and for reducing the measuring time, that the recording of the measured values may be undertaken at the same time, and thus the same conditions for all measurements are present in the sample at the measuring time. This is also advantageous, in particular, if during the measuring sequence, the shear forces exerted on the sample are altered according to predetermined criteria.

With the procedure according to the invention it is possible that the type of movement, in particular rotational speed, rotational direction, oscillation, speed, torque and/or motor current consumption of the first motor and of the further motor may be adjusted independently of one another.

A simple design of the rheometer according to the invention is produced when a combined control and/or evaluation unit is connected to the moment detector, to the measuring unit for determining the normal force, to the further moment detector and to the further measuring unit for determining the normal force.

For the evaluation, it is advantageous if a separate drive and regulating unit is assigned in each case to the motor and the further motor, which two units are controlled by the combined control unit, the two motors being able to be regulated independently of one another by means of the drive and regulating units which are independent of one another, in particular relative to the type of rotation, rotation, oscillation, speed, rotational speed, motor current consumption and/or rotational direction. It is advantageous in this connection if the two motors regulated by the drive and regulating units which are independent of one another, are able to be regulated in each case by taking into account the motion state of the respective other motor relative to the type of rotation, rotation, oscillation, speed, rotational speed, motor current consumption and/or rotational direction.

The cost of developing the rheometer is reduced when the measuring shaft and the further measuring shaft, the motor and the further motor, the moment detector and the further moment detector, the measuring unit and the further measuring unit and/or the two regulating units are in each case of the same design.

It is particularly advantageous for specific tests if it is provided that the first measuring part is formed by a cone with a flattened tip, which is divided by a cylindrical cut into two concentric parts, of which the conical ring is held fixedly in terms of rotation relative to the measuring shaft and the centrally located part may be rotated by the measuring shaft, that the further measuring part opposing the cone is formed by a circular plate, the diameter thereof corresponding at least to the diameter of the measuring part, and in that the measured values determined at the same time by the two moment detectors and the two measuring units are supplied to the combined control and evaluation unit and are used for determining the rheological properties of the sample.

For increasing the measuring accuracy and/or improving the measured results, it is advantageous if in each case a separate angular encoder is assigned to the first measuring shaft and the further measuring shaft for determining the rotational angle and/or the rotational speed and/or the speed.

The invention may be summarized as in the following two paragraphs:

The invention relates to a method for testing samples using a rheometer as well as such a rheometer in which a measuring shaft bearing a first measuring part is rotated by means of a motor for the rotation, the sample being introduced into a measuring gap formed by the first measuring part and a further measuring part, and the two measuring parts being rotated relative to one another, and by means of a moment detector the torque of the motor and by means of a first measuring unit the normal force exerted by the sample on the first measuring part.

According to the invention, it is provided that the first measuring part and the further measuring part mounted on a further measuring shaft for testing the sample are in each case rotated or oscillated at a predetermined speed independently of one another, or brought to a standstill, that at the same time or in rapidly succeeding intervals during the same measuring process, the torque and the normal force are determined by means of the first moment detector and the first measuring unit, and the normal force exerted by the sample on the further measuring part and/or the further measuring shaft and the torque exerted on the further measuring shaft by means of a further separate motor rotating said measuring shaft are determined by means of a further measuring unit and a further moment detector and in that said simultaneously determined measured values are supplied for evaluation.

Other features which are considered as characteristic for the invention are set forth in the appended claims.

Although the invention is illustrated and described herein as embodied in a rheometric method and rheometer for testing samples, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL
VIEWS OF THE DRAWING

DETAILED DESCRIPTION OF THE INVENTION

Figure 1:
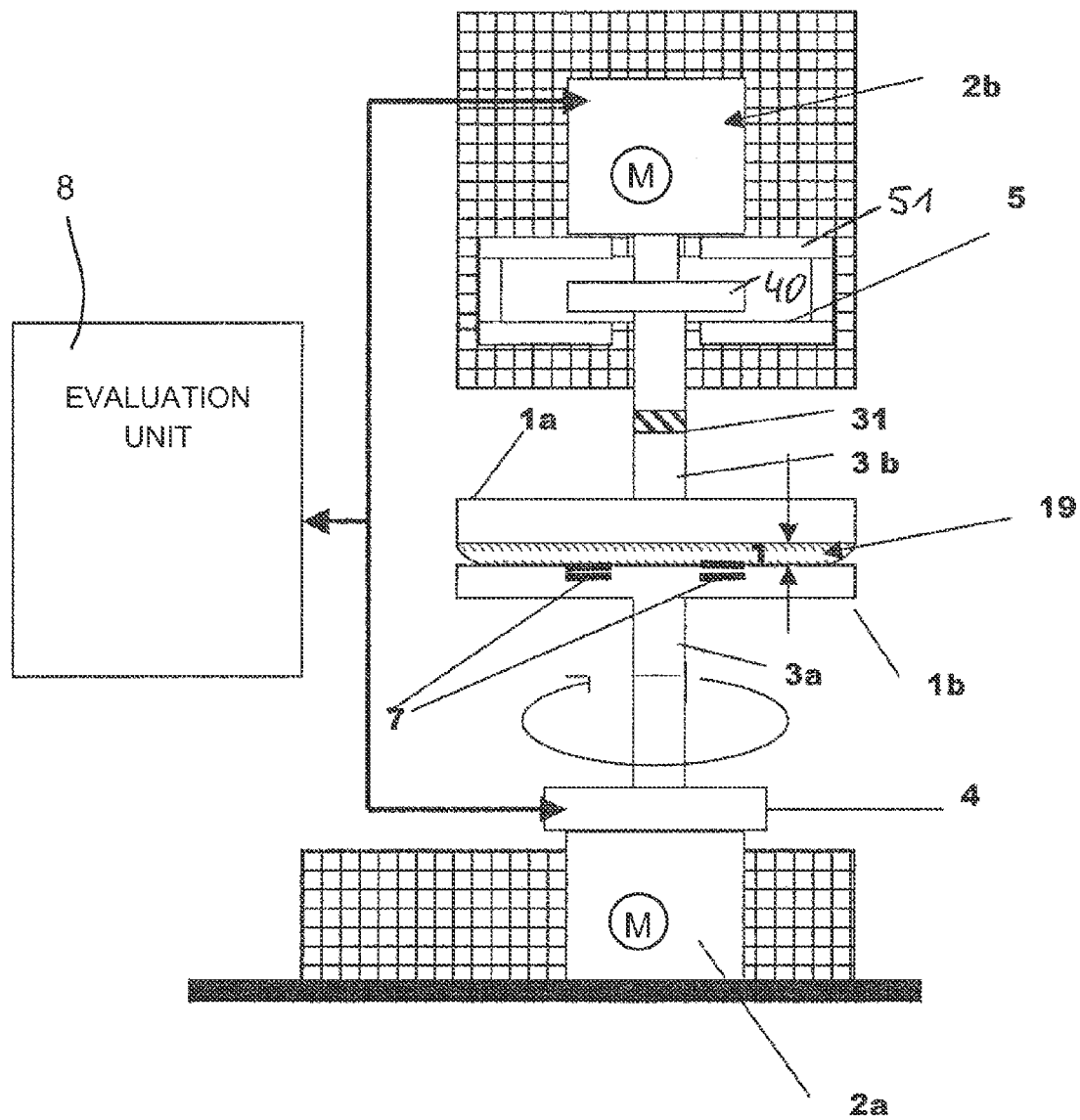
FIGS. 1 and 1A show the structural design of two prior art rheometers.
Figure 1A:
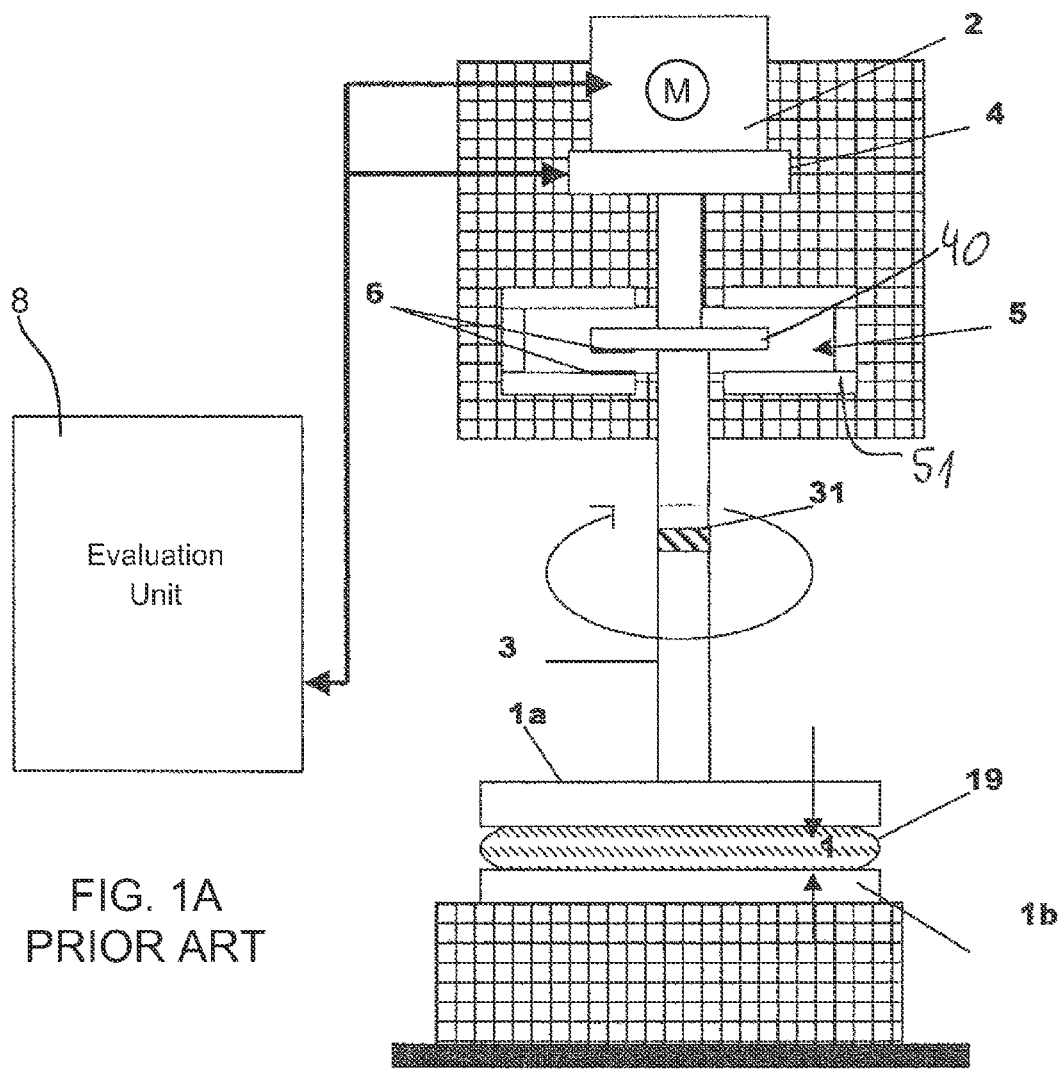

Referring now once more to the figures of the drawing in detail, FIGS. 1 and 1A illustrated two prior art rheometers. Similarly illustrated, FIG. 2 shows the configuration of a rheometer according to the invention, in which the sample 19 to be measured is introduced into a measuring chamber and/or measuring gap 1, which is formed between two measuring parts 1*a* and 1*b* that are height-adjustably mounted relative to one another and which have a defined geometry.

Figure 2:
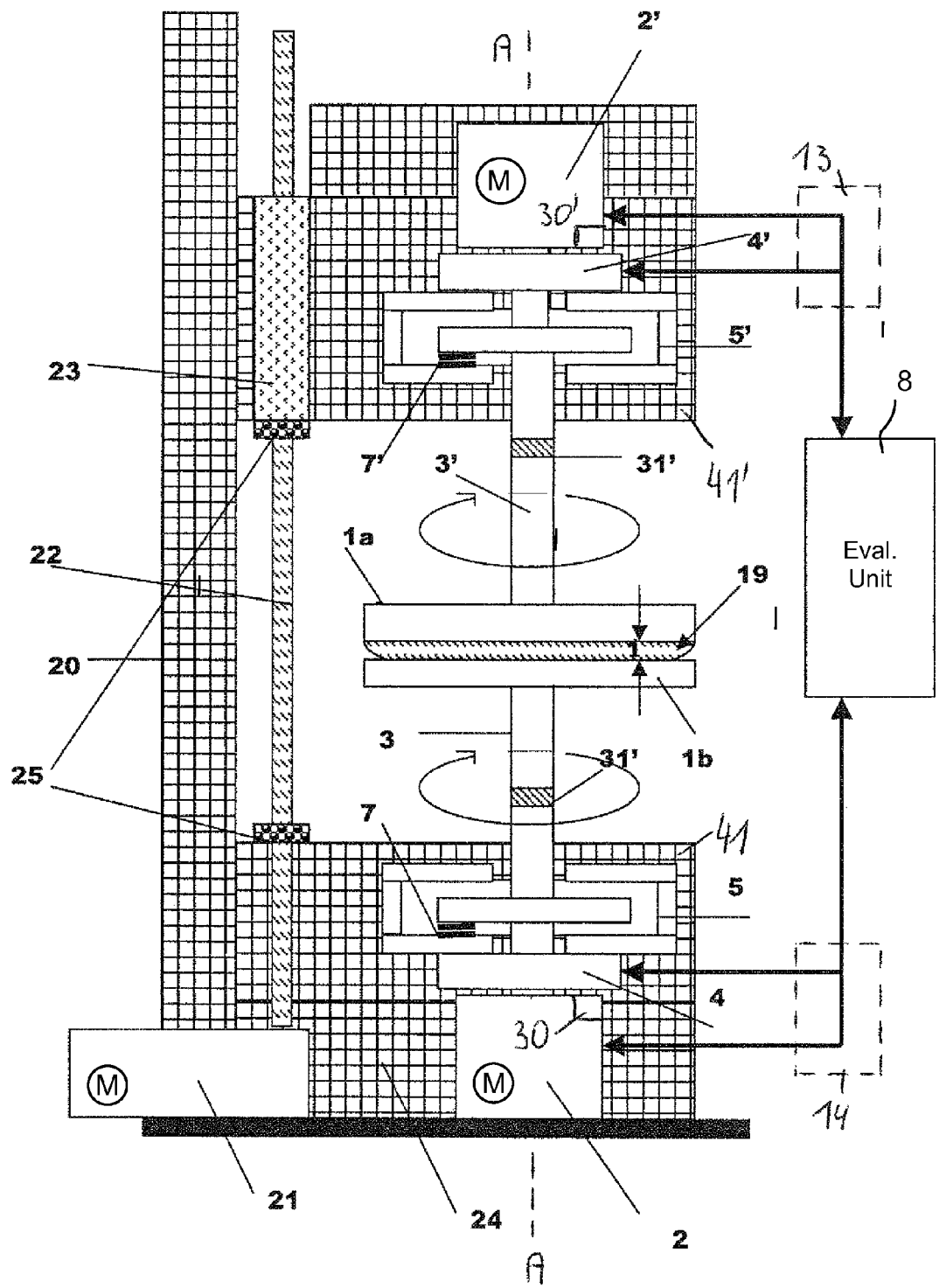
FIG. 2 is a diagrammatic side view of a rheometer according to the invention.

In the embodiment of FIG. 2 the upper measuring part 1*a* is held and/or driven by a measuring shaft and/or drive shaft 3'. A measuring and drive shaft 3 is provided for the lower measuring part 1*b*. The measuring and drive shafts 3, 3' hold the two measuring parts 1*a*, 1*b* relative to a common axis A centered at a predetermined gap height 1 and/or at a predetermined spacing relative to one another. Further, the shafts 3, 3' are mounted with as little friction as possible. The measuring parts 1*a*, 1*b* may advantageously be connected to the measuring and drive shafts 3, 3' via couplings 31'. The measuring and drive shafts 3, 3' may be mounted by way of air bearings 5, 5' in the housing of the rotary rheometer, and/or in corresponding bearing bodies 41, 41'. The measuring shafts 3, 3' and/or the measuring parts 1*a*, 1*b* are rotated by means of drive motors 2, 2' relative to one another and the acting torques are determined from the current consumption of the drive motors 2, 2'.

For determining the position of the measuring parts 1*a*, 1*b*, angular encoders 4, 4' are provided. These permit the rotational angle of the respective measuring part 1*a*, 1*b* to be determined and optionally via an additional time measurement the rotational speed and/or the speed to be determined, which values are supplied to an evaluation device 8, as is the determined value of the torque.

FIG. 2 shows a stand 20 by which the gap height 1 may be adjusted, by a torque motor 21 mounted on the stand 20 adjusting the height of the support 41' mounted on the upper adjusting part 23, by means of the adjusting unit formed by a screw spindle 22, relative to the lower adjusting part formed by a base plate 24 or relative to a support 41 which is mounted on the base plate 24.

The gap height 1 is adjusted by regulating the feed motor and/or torque motor 21 by means of the values measured by a unit 25 for measuring the spacing and/or length, which operates without contact and is arranged on the spindle 22. Also, other units for measuring the length, such as for example potentiometers, incremental displacement sensors, inductive measuring sensors and/or displacement sensors or dial gauges, may be used in order to determine the distance between the adjusted parts 23 and 24 and/or between the spindle nut and a fixed point on the stand 20 and/or on the base plate 24 forming the adjusting part, or between other fixed points. The actual spacing between the measuring parts 1*a*, 1*b* may also be measured in absolute terms by corresponding adjustment, taking into account the measured geometries on the vertical control system and/or feed system and/or adjustment system and/or on the adjusting unit or even relatively, i.e. for example by determining the torque increase when the measuring parts 1*a* and 1*b* come into contact with one another and the use of this starting point as a measured value for the gap-zero point.

Also the use of stepper motors is possible. In this connection, the position of the upper measuring part 1*a* is determined, based on a starting position and/or initial position of the spindle 22, by counting the rotary steps of the spindle clockwise and/or anti-clockwise and the multiplication thereof with the step angle where there is a defined advancing movement.

Thus under consistent environmental conditions, predetermined gap heights 1 may be accurately provided.

Figure 3:
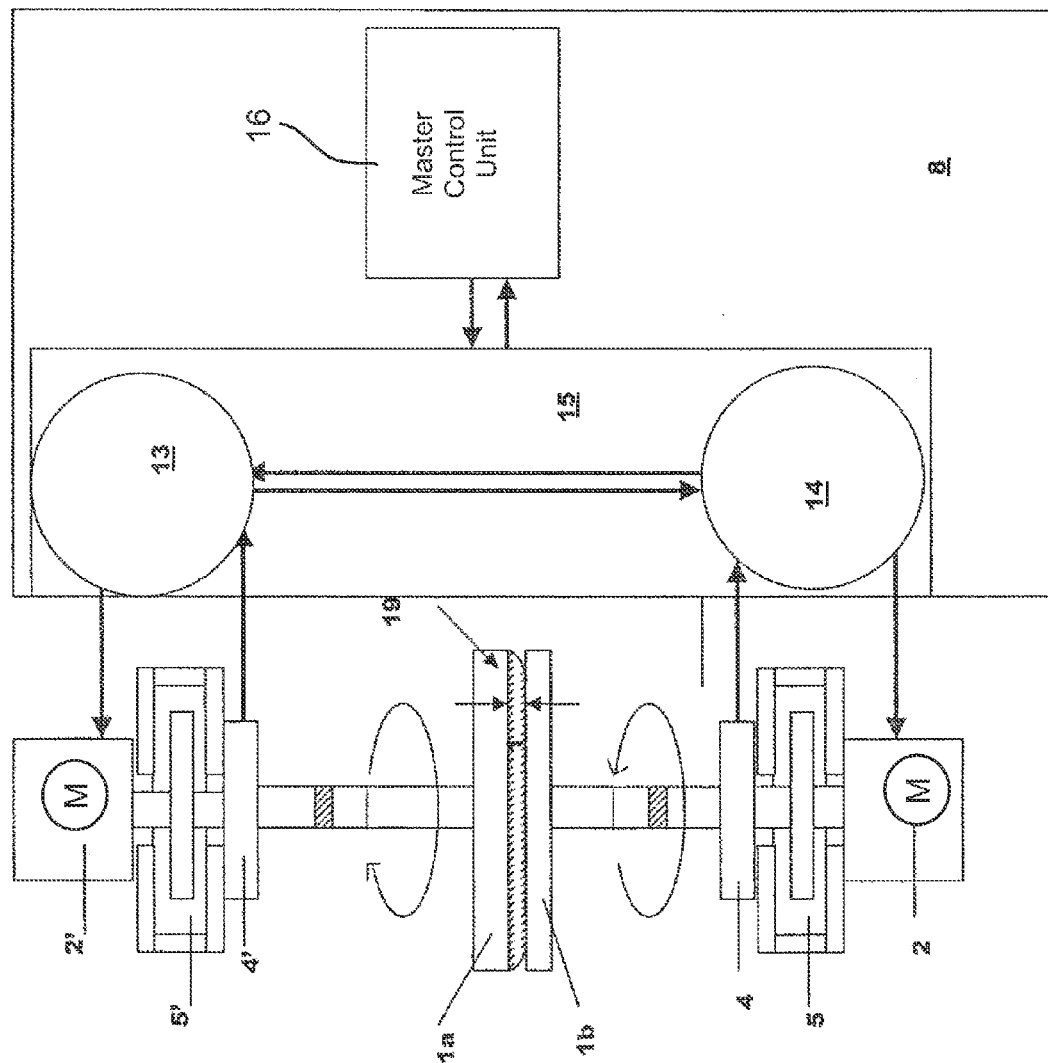
FIG. 3 shows schematically the control and the recording of the measured values in a rheometer according to the invention.

The drive motors 2, 2' are able to be regulated (i.e., closed-loop controlled) and controlled electronically. The torque of the motor 2 is determined by way of a moment detector 30 and the torque of the motor 2' is determined by way of a moment detector 30'. The control and evaluation unit 8 is connected to all measurement detectors and sensors, and evaluates the measured data obtained. In the rheometer according to the invention the regulating units 13, 14 which are assigned to the motor 2' and the motor 2, are combined to form a master control and regulating unit 15, as is shown in FIG. 3. This means that for each measuring and regulating period, both motors 2, 2' may be simultaneously used for measuring and driving tasks, mutually adjusted to one another by the underlying control program, and namely by controlling the master control unit 16.

The master control unit 16 predetermines the test parameters for the combined control and regulating unit 15, for example an overall speed, which is adjusted by mutual rotation of the upper and lower measuring parts. Additionally, the normal forces present on the two measuring parts 1*a*, 1*b* may be specifically determined, for which the corresponding measuring units 7, 7' for the normal forces are scanned. Normal forces are a measurement of the elastic components of real fluids and, in particular, play an important role in the field of polymer rheology; generally the effects which are present for highly viscous samples are significant and accordingly have to be taken into account.

As is revealed from FIGS. 2 and 3, the sample 19 is located in the measuring gap 1 between the upper measuring part 1*a* and the lower measuring part 1*b*. The drive and measuring motors 2, 2' drive the measuring shaft 3 and/or 3' respectively connected thereto. The rotation of the measuring shafts 3, 3' is detected by correspondingly assigned individual position sensors 4, 4' for the rotational angle and/or the speed. Advantageously, the measuring shafts 3, 3' are mounted in air bearings 5, 5' without friction in the respective supports 41, 41'. The measuring units 7, 7' are normally located in the respective air gap 5, 5'. Alternative variants with bearings which have as little friction as possible, such as for example magnetic bearings, are possible; the normal force may also be measured using, for example, strain gauges, suitable optical means or feedback of the motor.

According to FIG. 3, which illustrates the control and closed-loop control of the rheometer, the control and evaluation unit 8 comprises a closed-loop controller 13 for the upper drive motor 2' and a closed-loop controller 14 for the lower drive motor 2 as well as the master control and regulating unit 15, which monitors and/or regulates and/or controls the two controllers 13 and 14. The master control and evaluation unit 16 is connected to the unit 15, which may also serve as a user interface. Via this control and evaluation unit 16, the default values for carrying out the test may be entered, for example the speed of the drive motors 2, 2' may be predetermined. The closed-loop controller 13 regulates the type of movement and direction of movement of the drive and measuring motor 2' of the upper measuring part 1a according to the default values. The closed-loop controller 14 regulates the type of movement and direction of movement of the measuring part 1b underneath, irrespective of the rotation of the upper measuring part 1a, according to default values. The master closed-loop controller 15 permits, therefore, the monitoring and control of the two closed-loop controllers 13 and 14 and/or the two motor units using the motors 2, 2'. The predetermined test data are observed by simultaneous monitoring of the two controllers 13 and 14 and the motors 2, 2'.

It is possible, for example, to predetermine the speeds, and to measure the resulting torque and to detect therefrom the values for the viscosity. It is also possible to fix the position electronically of a motor 2 or 2' and/or the measuring part located thereon, and to rotate the respective other motor and/or the respective other measuring part and to predetermine the torque to be achieved. Alternatively, a specific speed may also be assigned to a motor, so that on the other motor a predetermined torque is to be reached. The correspondingly obtained measured values serve as a basis for determining the viscosity.

It is naturally possible to subject both motors 2, 2' optionally to oscillating movements and/or rotational movements. Thus measurements are possible in which one motor rotates and one motor oscillates or in which both motors may oscillate at the same or different amplitudes and frequencies and in different phase positions relative to one another. In any case, therefore, it is advantageous if the measured values read by the two regulating units 13 and 14 may be determined at the same time, because as a result the conditions prevailing in each case at this time in the sample may be fully taken into account.

It is particularly advantageous to use a rheometer according to the invention for determining the first and second normal force difference in highly elastic polymer melts.

Visco-elastic substances under shear exhibit a mixture of viscous and elastic behavior. In the shear test, normal forces NF are produced in the axial direction of the drive and measuring shafts 3, 3', which represent a measurement of the elastic component in the flow behavior. Under shear, normal forces of up to several 10 N may occur; the pressure and/or the normal force which act in the axial direction on the two measuring parts 1a, 1b is measured using known measuring detectors.

The normal force measured using conventional rheometer arrangements corresponds to the 1st normal stress difference $N_1$. Additionally, fluids with a high elastic component also exhibit a 2nd normal stress difference $N_2$. This is generally smaller (sometimes also negative) and plays an important role in the flow behavior of elastic fluids, for example the size and number of vortices which are formed in polymer melts depends on the 2nd normal force difference and thus significantly determines the behavior of these melts in the extruder. It is thus also very important to characterize polymers and other highly elastic melts/fluids with regard to $N_2$. $N_2$ is thus determined from the combination of a plurality of measurements. In the procedure according to the invention and/or the rheometer according to the invention, the use of a cone-plate geometry permits $N_2$ to be determined in only one measurement using different sample radii.

Figure 4:
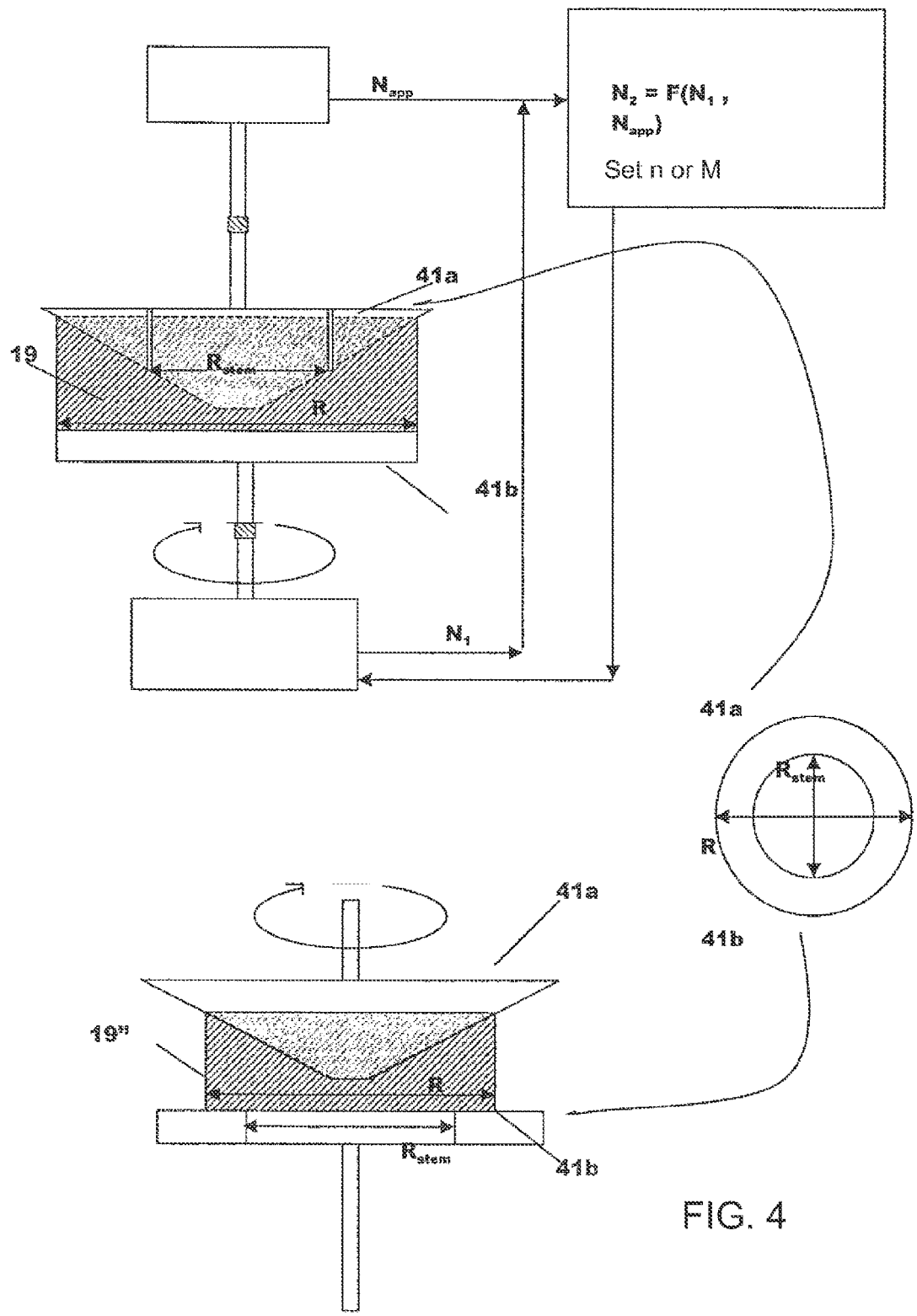
FIG. 4 shows schematically the execution of a specific measurement of samples using a rheometer according to the invention.

According to FIG. 4, the plate located underneath is rotated. The upper conical measuring part 41a is split. The outer conical ring 19 is fixed to the rheometer frame and/or stand 20 or the support 41. The inner conical punch measures the normal force $N_{app}$ on the inner part. If $N_1$ is known, $N_2$ may be calculated by $N_{app}$.

The following applies: $N_{app}=N_1+2(N_1+2\,N_2)\ln(R/R_{stem})$, where R is the outer radius and $R_{stem}$ is the inner radius.

By means of the rheometer according to the invention and the possibility of measuring normal forces acting on both measuring parts, $N_{app}$ on the segmented measured part and $N_1$ on the rotating measuring part applying the shear load are maintained simultaneously. Thus $N_2$ may be determined in a single measuring cycle. In this case, expediently the sample 19 with the radius R is positioned on the lower measuring part 41b and a shear load is exerted by rotation of the plate. The upper measuring part 41a is designed as a cone with a flat angle, and is radially divided into two, the inner radius $R_{stem}$ being available for measuring the normal force $N_{app}$, whilst the surrounding annular truncated cone with the radius $R_R$ being fixed to the rheometer frame and being stationary.

Instead of using a cone as the upper measuring part 41a, a two-part circular plate could also be used, the internal cylinder thereof being rotated relative to the outer circular ring.

The invention claimed is:

1. A rheometric method for testing samples, which comprises:
   providing a rheometer having a measuring shaft bearing a first measuring part, a first motor for rotating the first measuring shaft, a second measuring shaft bearing a second measuring part disposed to form a measuring gap together with the first measuring part, and a second motor for rotating the second measuring shaft;
   introducing a sample to be tested into the measuring gap formed between the first measuring part and the second measuring part;
   rotating or oscillating the first and second measuring parts relative to one another at a predetermined speed independently of one another, or bringing to a standstill independently of one another, and thereby determining a torque of the motor by way of a moment detector and detecting a normal force exerted by the sample on the first measuring part by way of a first measuring unit;
   simultaneously, or in rapidly successive intervals during the same measuring process, determining the torque and the normal force by way of the first moment detector and the first measuring unit, and determining a normal force exerted by the sample on the second measuring part and/or the second measuring shaft and the torque exerted on the second measuring shaft by the second motor rotating the second measuring shaft by way of a second measuring unit and a second moment detector; and
   supplying the simultaneously determined measured values for evaluation and outputting the evaluated test results pertaining to the respective sample.

2. The method according to claim 1, which comprises supplying the measured values for combined evaluation.

3. The method according to claim 1, wherein a type of movement of the first motor and a type of movement of the second motor are adjustable independently of one another and are adjusted by a common control unit.

4. The method according to claim 3, wherein the types of movement of the first and second motors are selected from the group consisting of rotational speed, rotational direction, oscillation, speed, torque, and motor current consumption.

5. The method according to claim 3, wherein the types of movement of the first and second motors are adjusted by taking into account a motion state of the respective other motor.

6. The method according to claim 1, which comprises rotating the first and second measuring parts in a common direction at different speeds.

7. A rheometer, comprising:
a first measuring shaft driven by a first motor and bearing a first measuring part;
a second measuring shaft driven by a second motor and bearing a second measuring part disposed to form a measuring gap for a sample together with said first measuring part;
a first moment detector for detecting a torque of said first motor;
a first measuring unit for determining a normal force exerted by the sample on said first measuring shaft and/or on said first measuring part;
wherein a rotational axis of said second measuring shaft is aligned with a rotational axis of said first measuring shaft;
a second moment detector for determining a torque exerted by said second motor; and
a second measuring unit for determining a normal force exerted by the sample on said second measuring part and/or on said second measuring shaft.

8. The rheometer according to claim 7, which further comprises a combined control and/or evaluation unit connected to said first and second moment detectors for determining the torques, and to said first and second measuring units for determining the normal forces.

9. The rheometer according to claim 7, which further comprises separate and mutually independent drive and regulating units respectively assigned to each said first motor and said second motor, wherein said units are connected to and controlled by a combined control unit connected to said first and second moment detectors for determining the torques, and said first and second motors are regulatable independently of one another by way of said drive and regulating units.

10. The rheometer according to claim 9, wherein said drive and regulating units are configured to independently drive said first and second motors with regard to a type of rotation, a rotation, an oscillation, a speed, a rotational speed, a motor current consumption, and/or a rotational direction.

11. The rheometer according to claim 9, wherein said drive and regulating units are configured to regulate said first and second motors in each case by taking into account a motion state of the respective other motor relative to the type of rotation, rotation, oscillation, speed, rotational speed, motor current consumption, and/or rotational direction.

12. The rheometer according to claim 7, wherein one or more of the following are true: said first and second measuring shaft have a common design, said first and second motors have a common design, said first moment detector and said second moment detector have a common design, said first measuring unit and said second measuring unit have common design, or said first and second regulating units have a common design.

13. The rheometer according to claim 7, wherein:
said first measuring part is a cone with a flattened tip, divided by a cylindrical cut into two concentric parts with a conical ring held fixedly in terms of rotation relative to said first measuring shaft and a centrally located part rotatable by said first measuring shaft;
said second measuring part opposite said cone is formed by a circular plate having a diameter corresponding at least to a diameter of said cone of said first measuring part; and
the measured values determined by said first and second moment detectors and said two measuring units at the same time are supplied to the combined control and evaluation unit and are used for determining rheological properties of the sample.

14. The rheometer according to claim 13, configured to determine a viscosity of the sample under test.

15. The rheometer according to claim 7, which comprises a first angular encoder assigned to said first measuring shaft and a second angular encoder, separate from said first encoder, assigned to said second measuring shaft for determining at least one of a rotational angle, a rotational speed, or a speed of the respective measuring shaft.

* * * * *